(12) United States Patent
Tuohy et al.

(10) Patent No.: US 12,370,244 B2
(45) Date of Patent: *Jul. 29, 2025

(54) BREAST CANCER VACCINE

(71) Applicant: The Cleveland Clinic Foundation, Cleveland, OH (US)

(72) Inventors: Vincent K. Tuohy, Broadview Heights, OH (US); Justin M. Johnson, Willoughby Hills, OH (US); Ritika Jaini, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/063,999

(22) Filed: Dec. 9, 2022

(65) Prior Publication Data

US 2024/0075115 A1    Mar. 7, 2024

Related U.S. Application Data

(60) Continuation of application No. 16/584,718, filed on Sep. 26, 2019, now Pat. No. 11,547,749, which is a division of application No. 14/851,674, filed on Sep. 11, 2015, now Pat. No. 10,463,724, which is a continuation of application No. 14/132,962, filed on Dec. 18, 2013, now Pat. No. 9,446,104, which is a division of application No. 13/157,990, filed on Jun. 10, 2011, now Pat. No. 9,125,848.

(60) Provisional application No. 61/353,825, filed on Jun. 11, 2010, provisional application No. 61/353,464, filed on Jun. 10, 2010, provisional application No. 61/353,470, filed on Jun. 10, 2010.

(51) Int. Cl.
A61K 39/00 (2006.01)
A61K 40/11 (2025.01)
A61K 40/42 (2025.01)

(52) U.S. Cl.
CPC .......... *A61K 39/0011* (2013.01); *A61K 40/11* (2025.01); *A61K 40/42* (2025.01); *A61K 2039/545* (2013.01); *A61K 2039/55577* (2013.01); *A61K 2039/572* (2013.01); *A61K 2039/812* (2018.08); *A61K 2239/49* (2023.05)

(58) Field of Classification Search
CPC .......................... A61K 39/0011; A61K 40/42
See application file for complete search history.

(56) References Cited

U.S. PATENT DOCUMENTS

| 6,812,339 | B1 | 11/2004 | Venter et al. |
| 9,125,848 | B2 | 9/2015 | Tuohy et al. |
| 9,327,026 | B2 | 5/2016 | Tuohy |
| 2006/0153861 | A1 | 7/2006 | Scheinberg |
| 2007/0099833 | A1 | 5/2007 | Rosen et al. |
| 2012/0003254 | A1 | 1/2012 | Tuohy |

FOREIGN PATENT DOCUMENTS

| JP | 2004-534088 A | 11/2004 |
| JP | 2006-076961 | 3/2006 |
| JP | 2006-522828 A | 10/2006 |
| JP | 2009-500298 A | 7/2009 |
| WO | 2003/003985 A2 | 1/2003 |
| WO | 2004/091507 A2 | 10/2004 |
| WO | 2005/005615 A2 | 1/2005 |
| WO | 2006/138675 A2 | 12/2006 |
| WO | WO-2008/058547 A2 | 5/2008 |

OTHER PUBLICATIONS

Lee et al. Increased Vaccine-Specific T Cell Frequency After Peptide-Based Vaccination Correlates with Increased Susceptibility to In Vitro Stimulation But Does Not Lead to Tumor Regression. Journal of Immunology. 1999; 163: 6292-6300 (Year: 1999).*
Zaks et al. Immunization with a peptide epitope (p. 369-377) from Her-2/neu leads to peptide-specific cytotoxic T lymphocytes that fail to recognize Her-2/neu + tumors. Cancer Research. 1998; 58: 4902-4908 (Year: 1998).*
Gao et al. Tumor vaccination that enhances antitumor T-cell responses does not inhibit the growth of established tumors even in combination with interleukin-12 treatment: the importance of inducing intratumoral T-cell migration. Journal of Immunotherapy. 2000; 23: 643-653 (Year: 2000).*
Rosenberg et al. Tumor Progression Can Occur despite the Induction of Very High Levels of Self/Tumor Antigen-Specific CD8* T Cells in Patients with Melanoma. J. Immunol. 2005; 175: 6169-6176 (Year: 2005).*
Harlin et al. Tumor progression despite massive influx of activated CD8* T cells in a patient with malignant melanoma ascites. Cancer Immunol. Immunother. 2006; 55: 1185-1197 (Year: 2006).*

(Continued)

*Primary Examiner* — Vanessa L. Ford
*Assistant Examiner* — Sandra Carter
(74) *Attorney, Agent, or Firm* — Casimir Jones, S.C.; Jason R. Bond

(57) ABSTRACT

Compositions and methods for immunization against human breast cancer are disclosed. A breast cancer vaccine comprises an immunogenic polypeptide comprising human α-lactalbumin.

7 Claims, 18 Drawing Sheets

Specification includes a Sequence Listing.

(56) References Cited

OTHER PUBLICATIONS

Kesaraju. Development and characterization of murine experimental autoimmune mastitis. ProQuest Dissertations and Theses, Retrieved from http://search.proquest.com/docview/304763025?accountid=14753 (304763025) 2007 (Year: 2007).*

Bartkova, et al., "Lack of beta-Casein production by human breast tumours revealed by monoclonal antibodies," Eur J Cancer Clin Oncol, 23(10): 1557-1563 (1987).

Bergers, et al., "Extrinsic regulators of epithelial tumor progression: metalloproteinases," Curr Opin Genet Dev, 10(1): 120-127 (2000).

Bodey, et al., "Failure of cancer vaccines: the significant limitations of this approach to immunotherapy," Anticancer Res, 20(4): 2665-2676 (1999).

Bonuccelli, et al., "The milk protein alpha-casein functions as a tumor suppressor via activation of STAT1 signaling, effectively preventing breast cancer tumor growth and metastasis," Cell Cycle, 11(21): 3972-3982 (2012).

Bowie, et al., "Deciphering the Message in Protein Sequences: Tolerance to Amino Acid Substitutions," Science, 247: 1306-1310 (1990).

Charpin, et al., "Kappa casein, lactalbumin and GCDFP 70 localization in human breast carcinomas: an immunohistochemical study using the avidin-biotin-peroxidase complex method," Med Oncol Tumor Pharmacother, 2(2): 103-112 (1985).

Dempsey, et al., "Development of monoclonal antibodies to the human breast carcinoma cell line PMC42," J Natl Cancer Inst, 77(1): 1-15 (1986).

Dennis, "Cancer: off by a whisker," Nature, 442(7104): 739-741 (2006).

Gao, et al., "Tumor vaccination that enhances antitumor T-cell responses does not inhibit the growth of established tumors even in combination with interleukin-12 treatment: the importance of inducing intratumoral T-cell migration," J Immunother, 23(6): 643-653 (2000).

Gura, "Systems for Identifying New Drugs are Often Faulty," Science, 278(5340): 1041-1042 (1997).

Hall, et al., "alpha-Lactalbumin is not a marker of human hormone-dependent breast cancer," Nature, 290: 602-604 (1981).

Harlin, et al., "Tumor progression despite massive influx of activated CD8+ T cells in a patient with malignant melanoma ascites," Cancer Immunol Immunother, 55(10): 1185-1197 (2006).

Herbert, et al., "Casein and alpha-lactalbumin detection in breast cancer cells by immunocytochemistry," Cancer Res, 38(8): 2221-2223 (1978).

Hudis, et al., "Triple Negative Breast Cancer: An Unmet Medical Need," Oncologist, 16(1): 1-11 (2011).

International Search Report for International Application PCT/US2013/036607 dated Aug. 6, 2013.

Jaini, et al., "An autoimmune-mediated strategy for prophylactic breast cancer vaccination," Nature Med, 16(7): 799-803 (2010).

Kelland, ""Of mice and men": values and liabilities of the athymic nude mouse model in anticancer drug development," Eur J Cancer, 40(6): 827-836 (2004).

Kesaraju, et al., "Development and characterization of murine experimental autoimmune mastitis," ProQuest Dissertations and Theses, retrieved from http://search.proquest.com/docview/304763025?accountid=14753.

Kesaraju, et al., "Experimental autoimmune breast failure: a model for lactation insufficiency, postnatal nutritional deprivation, and prophylactic breast cancer vaccination," Am J Pathol, 181(3): 775-784 (2012).

Kunz, et al., "Human-milk proteins: analysis of casein and casein subunits by anion-exchange chromatography, gel electrophoresis, and specific staining methods," Am J Clin Nutr, 51(1): 37-46 (1990).

Lazar, et al., "Transforming Growth Factor ox: Mutation of Aspartic Acid 47 and Leucine 48 Results in Different Biological Activities," Mol Cell Biol, 8(3): 1247-1252 (1988).

Lee, et al., "Increased vaccine-specific T cell frequency after peptide-based vaccination correlates with increased susceptibility to in vitro stimulation but does not lead to tumor regression," J Immunol, 163(11): 6292-6300 (1999).

Lollini, et al., "Cancer immunoprevention: tracking down persistent tumor antigens," Trends Immunol, 24(2): 62-66 (2003).

Lollini, et al., "New target antigens for cancer immunoprevention," Curr Cancer Drug Targets, 5(3): 221-228 (2005).

Monaco, et al., "Casein production by human breast cancer," Cancer Res, 37(3): 749-754 (1977).

Motrich, et al., "Cow's milk stimulated lymphocyte proliferation and TNFalpha secretion in hypersensitivity to cow's milk protein," Clinical Immunology, 109(2): 203-211 (2003).

Pancino, et al., "Characterization and distribution in human tissues of a glycoproteic antigen defined by monoclonal antibody 1BE12 raised against the human breast cancer cell line T47D," Cancer Res, 50(22): 7333-7342 (1990).

Ragupathi, "Antibody inducing polyvalent cancer vaccines," Cancer Treat, 123: 157-180 (2005).

Richmond, et al., "Mouse xenograft models vs. GEM models for human cancer therapeutics," Disease Models and Mechanisms, 1(2-3): 78-82 (2008).

Rosenberg, et al., "Tumor progression can occur despite the induction of very high levels of self/tumor antigen-specific CD8+ T cells in patients with melanoma," J Immunol, 175(9): 6169-6176 (2005).

Saijo, et al., "What are the reasons for negative phase III trials of molecularL targetL based drugs?" Cancer Sci, 95(10): 772-776 (2004).

Sawyers, et al., "The cancer biomarker problem," Nature, 452(7187): 548-552 (2008).

Simickova, et al., "Polyclonal antibodies to human milk caseins," J Dairy Res, 58(1): 115-125 (1991).

Slinghuff, et al., "Melanomas with concordant loss of multiple melanocytic differentiation proteins: immune escape that may be overcome by targeting unique or undefined antigens," Cancer Immunol Immunother, 48(12): 661-672 (2000).

Smith, et al., "Expression of pregnancy-specific genes in preneoplastic mouse mammary tissues from virgin mice," Cancer Res, 44(8): 3426-3437 (1984).

Tassone, et al., "Loss of BRCA1 function increases the antitumor activity of cisplatin against human breast cancer xenografts in vivo," Cancer Biol Ther, 8(7): 648-653 (2009).

Tellez, et al., "Characterization of immune-active peptides obtained from milk fermented by Lactobacillus helveticus," J Dairy Res, 77(2): 129-136 (2010).

Thompson, et al., "A human breast tissue-associated antigen detected by a monoclonal antibody," J Natl Cancer Inst, 70(3): 409-419 (1983).

Vohr, et al., "Persistent beneficial effects of breast milk ingested in the neonatal intensive care unit on outcomes of extremely low birth weight infants at 30 months of age," Pediatrics, 120(4): e953-e959 (2007).

Walker, et al., "The demonstration of alpha lactalbumin in human breast carcinomas," J Pathol, 129(1): 37-42 (1979).

Whisstock, et al., "Prediction of protein function from protein sequence and structure," Quarterly Rev Biophys, 36(3): 307-340 (2007).

Zaks, et al., "Immunization with a peptide epitope (p. 369-377) from HER-2/neu leads to peptide-specific cytotoxic T lymphocytes that fail to recognize HER-2/neu+ tumors," Cancer Res, 58(21): 4902-4908 (1998).

Bartkova et al., "Lack of beta-casein production by human breast tumours revealed by monoclonal antibodies," Eur. J. Cancer Clin. Oncol., Oct. 1987; 23 (10): 1557-63.

Bergers et al., "Extrinsic regulators of epithelial tumor progression: metalloproteinases," Current Opinion in Genetics and Development, 2000; 10(1): 120-127.

Bielinska et al., "Induction of Th17 cellular immunity with a novel nanoemulsion adjuvant," Crit Rev Immunol., 2010, vol. 30, pp. 189-199.

Bodey et al., "Failure of cancer vaccines: the significant limitations of this approach to immunotherapy," Anticancer Research, 2000; 20: 2665-2676.

(56) References Cited

OTHER PUBLICATIONS

Charpin et al., "Kappa casein, lactalbumin and GCDFP 70 localization in human breast carcinomas: an immunohistochemical study using the avidin-biotin-peroxidase complex method," Med. Oncol. Tumor Pharmacother., 1985; 2 (2): 103-12.

Cohen et al., "Tumor-Associated Antigens in Breast Carcinomas Prognostic Significance," Cancer, 1987, 60: 1294-1298.

Cunha-Neto E., "MHC restricted antigen presentation and recognition: constraints on gene, recombinant and peptide vaccines in humans", Brazilian J of Medical and Biological Research, 1999, 32: 199-205.

Declaration under 37 CFR 1.132 of Dr. Vincent Tuohy, including Exhibits (filed Jun. 10, 2011 in U.S. Appl. No. 13/157,990).

Dempsey et al., "Development of monoclonal antibodies to the human breast carcinoma cell line PMC42," J. Natl. Cancer Inst, Jul. 1986; 77 (1): 1-15.

Dennis, "Cancer: off by a whisker," Nature, Aug. 17, 2006; 442(7104): 739-741.

Gao et al., "Tumor vaccination that enhances antitumor T-cell responses does not inhibit the growth of established tumors even in combination with interleukin-12 treatment: the importance of inducing intratumoral T-cell migration," Journal of Immunotherapy, 2000; 23(6): 643-653.

Gura, "Systems for identifying new drugs are often faulty," Science. 1997; 278: 1041-1042.

Herbert et al., "Casein and alpha-lactalbumin detection in breast cancer cells by immunocytochemistry," Cancer Res., Aug. 1978; 38 (8): 2221-3.

International Search Report and Written Opinion for International Application PCT/US2013/036607 dated Jul. 30, 2013.

International Search Report and Written Opinion for International Application No. PCT/US2016/050159 dated Dec. 8, 2016.

International Search Report and Written Opinion for International Application No. PCT/US2016/060120 dated Feb. 6, 2017.

Kaetzel et al., "Immunochemical Characterization with Monoclonal Antibodies of Three Major Caseins and Alpha-Lactalbumin from Rat Milk," J Dairy Sci., 1984, 67: 64-75.

Kelland, "Of mice and men: values and liabilities of the athymic nude mouse model in anticancer drug development," Eur. J. Cancer., Apr. 2004; 40 (6): 827-836.

Kojima, "Oral Challenge with Cow's Milk in Patients with IgA Nephropathy—Estimation of Serum Antibodies to Cow's Milk Protein," Jpn J Nephrol., 1991 XXXIII(10): 961-971. (Partial translation included.).

Kunz et al., "Human-milk proteins: analysis of casein and casein subunits by anion-exchange chromatography, gel electrophoresis, and specific staining methods," Am. J. Clin. Nutr., Jan. 1990; 51 (1): 37-46.

Lollini et al., "Cancer immunoprevention: tracking down persistent tumor antigens," Trends Immunol., Feb. 2003; 24 (2): 62-66.

Lollini et al., "New target antigens for cancer immunoprevention" Curr. Cancer Drug Targets, May 2005; 5 (3): 221-228.

Marcus, "Immunologic aspects of cancer of the breast", A.J.C.P., 1975, vol. 64, p. 786-791.

Monaco et al.,"Casein production by human breast cancer," Cancer Res., Mar. 1977; 37 (3): 749-54.

Motrich et al., "Cow's milk stimulated lymphocyte proliferation and TNFalpha secretion in hypersensitivity to cow's milk protein," Clinical Immunology, 2003, 109(2): 203-211.

Nakano et al., "Effect of casein phosphopeptide as oral immune adjuvant," Summary of the 2002 Annual Meeting of the Japan Society for Bioscience, Biotechnology and Agrochemistry, p. 256, "4-3Ga01". (Partial English translation Included.).

Pancino et al., "Characterization and distribution in human tissues of a glycoproteic antigen defined by monoclonal antibody 1BE12 raised against the human breast cancer cell line T47D," Cancer Res., Nov. 15, 1990; 50 (22): 7333-42.

Russian Office Action Summary (translated in English) in RU 2014145870 dated Mar. 23, 2017.

Saijo, "What are the reasons for negative phase III trials of molecular-target-based drugs," Cancer Sci., Oct. 2004; 95 (10): 772-776.

Simickova et al., "Polyclonal antibodies to human milk caseins," J. Dairy Res. Feb. 1991; 58 (1): 115-25.

Slingluff et al.,"Melanomas with concordant loss of multiple melanocytic differentiation proteins: immune escape that may be overcome by targeting unique or undefined antigens," Cancer Immunol. Immunother., Mar. 2000; 48 (12): 661-672.

Smith et al., "Expression of pregnancy-specific genes in preneoplastic mouse mammary tissues from virgin mice," Cancer Res. Aug. 1984; 44 (8): 3426-37.

Suminami et al., "In situ interleukin-4 gene expression in cancer patients treated with genetically modified tumor vaccine," J. Immunother. Emphasis Tumor Immunol., May 1995; 17 (4): 238-48.

Tassone et al., "Loss of BRCA1 function increases the antitumor activity of cisplatin against human breast cancer xenografts in vivo," Cancer Biol Ther., Apr. 2009; 8 (7): 1-6.

Tellez et al., "Characterization of immune-active peptides obtained from milk fermented by Lactobacillus helveticus," J Dairy Res., 2010, 77(2): 129-136.

Thompson et al., "A human breast tissue-associated antigen detected by a monoclonal antibody," J. Natl. Cancer Inst., Mar. 1983; 70(3): 409-19.

Vohr et al., "Persistent beneficial effects of breast milk ingested in the neonatal intensive care unit on outcomes of extremely low birth weight infants at 30 months of age," Pediatrics, Oct. 2007; 120 (4): e953-9.

Yakubke et al., "Amino acids, peptides, proteins," M Mir, 1985, pp. 92-94. (English translation of Russian Office action mentioning this reference is included—NPL reference 28.).

* cited by examiner

BREAST CANCER VACCINE

GOVERNMENT RIGHTS

This invention was made with government support under grant numbers AI051837, DC006422, and CA14035 awarded by the National Institutes of Health. The government has certain rights in the invention.

SEQUENCE LISTING

The text of the computer readable sequence listing filed herewith, titled "39540-308 SEQUENCE LISTING", created Oct. 11, 2022, having a file size of 1,990 bytes, is hereby incorporated by reference in its entirety.

TECHNICAL FIELD

The present disclosure generally pertains to the fields of immunology and oncology. More particularly, the present disclosure pertains to the prevention or treatment of breast cancer by vaccination.

BACKGROUND AND SUMMARY

Breast cancer is responsible for the second overall cause of cancer-related deaths among women. Currently, prevention of breast cancer predominantly involves reducing modifiable risks including early detection through physical examination and mammograms, avoidance of unnecessary post-menopausal hormone therapy, reduction in alcohol consumption, loss of weight, increase in physical activity, and genetic testing for mutations of the breast cancer type 1 and type 2 susceptibility genes (BRCA1 and BRCA2, respectively). More aggressive approaches in high risk patients include chemoprevention with tamoxifen, raloxifene, and aromatase inhibitors as well as prophylactic bilateral mastectomy and oophorectomy.

Despite the profound health risk of breast cancer and inadequacy of preventative efforts, an immunotherapy for breast cancer has not been developed as an integral part of the standard of care. Tumor-specific antigens have long provided less than optimal results as targets for cancer vaccination. The overall goal of cancer vaccination has traditionally been to boost the latent immune response to tumor-specific antigens. Approaches have included cell-based protocols involving immunization with whole autologous or allogeneic tumors, as well as antigen-based strategies involving immunization with proteins or peptides overexpressed in tumors and underexpressed in normal tissues. The human epidermal growth factor receptor 2 (HER2) and mucin (MUC1) are the predominant antigens used in human breast cancer vaccine trials. Although vaccination using these antigens may demonstrate tumor reducing effects, neither antigen provides any tissue or tumor specificity since both are expressed in a variety of normal tissues and tumors. Thus, the lack of inherent tissue specificity of HER2 and MUC1 targeted immunity may ultimately lead to substantial systemic autoimmune sequelae if a robust immune response manifests.

A full-strength autoimmune attack sufficient to induce targeted breast failure can provide effective therapy against established breast malignancies if the target antigen is constitutively expressed in breast tumors. Moreover, if the selected target antigen is expressed in normal breast tissue under conditions that are easily avoidable, then the vaccine may provide safe and effective protection against the development of breast cancer.

Human alpha-lactalbumin (α-lactalbumin) is a conditionally expressed, breast specific differentiation protein found in the majority of breast malignancies. As an integral differentiation protein involved in regulation of lactose biosynthesis, expression of α-lactalbumin is breast-specific and conditionally dependent on lactation for its expression and synthesis. Human α-lactalbumin is also constitutively overexpressed in the majority of breast tumors, is breast specific, and is sufficiently immunogenic to induce an effective proinflammatory immune response. Thus, immunization against human α-lactalbumin offers a safe and effective vaccination strategy for the prevention of breast cancer.

BRIEF DESCRIPTION OF THE DRAWINGS

FIG. 7D right panel) that are enriched by magnetic bead separation from α-lactalbumin primed LNC. All error bars show ±SEM. Each* indicates a statistically significant difference.

DETAILED DESCRIPTION

Figure 1A:
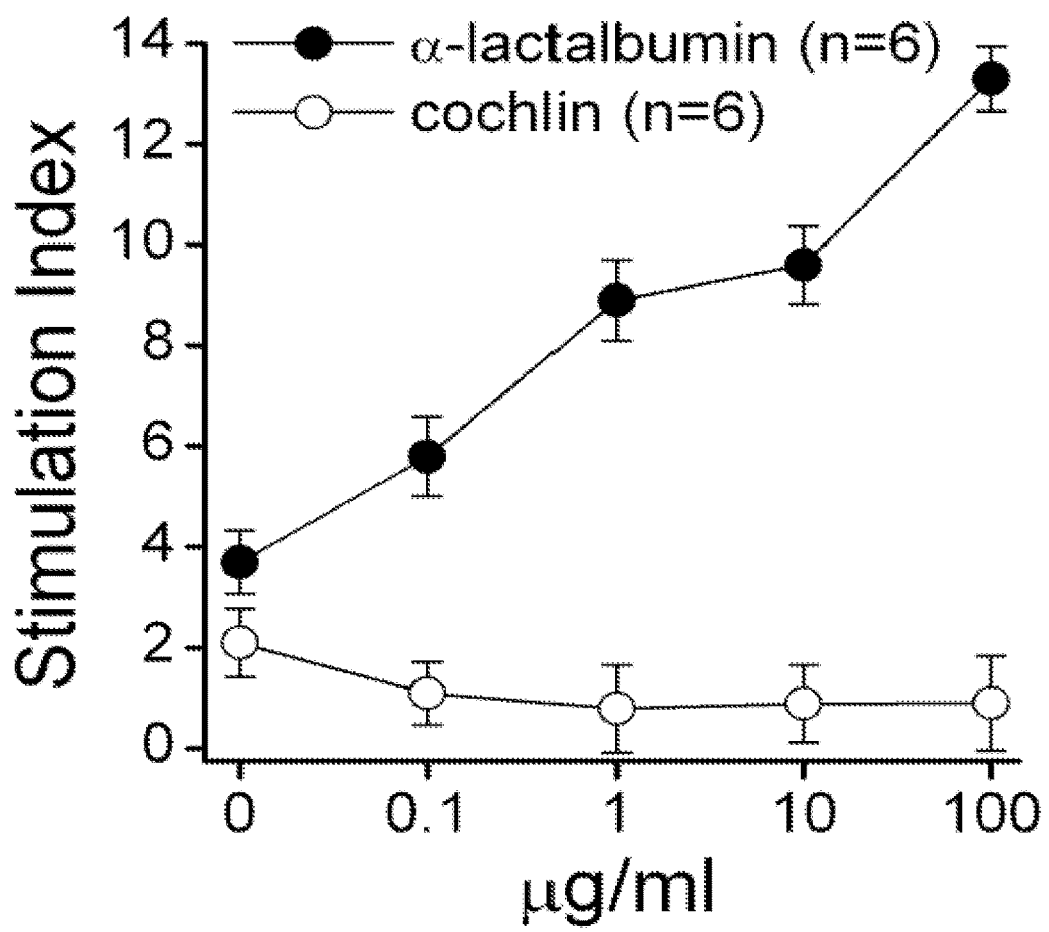
FIG. 1A shows the immunogenicity of recombinant mouse α-lactalbumin. Lymph node cells are evaluated 10 days after immunization of SWXJ female mice with α-lactalbumin and show recall responses that are a) antigen-specific to recombinant mouse α-lactalbumin but not to recombinant human cochlin over a dose range; b) elicited from both purified CD4+ and CD8+ T cells in response to 25 µg/ml α-lactalbumin (see FIG. 1B); and c) consistent with a proinflammatory type 1 cytokine profile with high production of IFNγ and IL-2 and low production of the type 2 cytokines, IL-4, IL-5, and lactalbumin (see FIG. 1C). All error bars show ±SEM.

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the scope of the invention.

In one embodiment, a human breast cancer vaccine comprising an immunogenic polypeptide is disclosed. The immunogenic polypeptide comprises human α-lactalbumin according to the amino acid sequence:

kqftkcelsq llkdidgygg ialpelictm fhtsgydtqa ivennestey glfqisnklw ckssqvpqsr nicdiscdkf lddditddim cakkildikg idywlahkal ctekleqwlc ekl (SEQ ID NO: 1).

It is appreciated that human α-lactalbumin is processed in vivo by proteases to smaller peptide fragments, which are able to bind to MHC class I and/or MHC class II molecules on antigen presenting cells. Subsequently, T-cell receptors recognize and bind to the MHC molecule to which the peptide is bound, forming the primary signal that initiates an immune response.

In one embodiment, the vaccine further comprises an adjuvant and a pharmaceutically acceptable carrier. As used herein, the term "adjuvant" refers to an agent that stimulates the immune system and increases the response to a vaccine. Vaccine adjuvants are well-known to those of skill in the art. Illustratively, GPI-0100 is a suitable adjuvant for a vaccine. As used herein, the term "carrier" refers to an ingredient other than the active component(s) in a formulation. The choice of carrier will to a large extent depend on factors such as the particular mode of administration or application, the effect of the carrier on solubility and stability, and the nature of the dosage form. Pharmaceutically acceptable carriers for polypeptide antigens are well known in the art.

In one embodiment, the vaccine is administered prophylactically to prevent breast cancer. In one illustrative aspect, the vaccine is administered to non-lactating women at risk for developing breast cancer.

In one embodiment, the vaccine is administered to inhibit tumor cell expansion.

The vaccine may be administered prior to or after the detection of breast tumor cells in a patient Inhibition of tumor cell expansion is understood to refer to preventing, stopping, slowing the growth, or killing of tumor cells.

In one illustrative aspect, T cells of the human immune system are activated after administration of an immunogenic composition comprising human α-lactalbumin. The activated T cells may be CD4+ and/or CD8+.

In one embodiment, after administration of a vaccine comprising human α-lactalbumin, a proinflammatory response is induced by subsequent encounter of immune cells with α-lactalbumin. The proinflammatory immune response comprises production of proinflammatory cytokines and/or chemokines, for example, interferon gamma (IFNγ) and/or interleukin 2 (IL-2). Proinflammatory cytokines and chemokines are well known in the art.

It is to be appreciated that when the breast cancer vaccine is administered to patients whose breast tissue is not actively producing human α-lactalbumin in appreciable quantities (i.e. a non-lactating female, or a female devoid of α-lactalbumin producing breast tumor cells), immunization with human α-lactalbumin does not elicit a substantial inflammatory immune response (i.e. that is capable of causing breast tissue failure) in breast tissue. Subsequent encounter with human α-lactalbumin, such as that expressed by cells of a developing tumor elicits a recall response by the immune system. The recall response includes, but is not limited to, an increase in the production of proinflammatory cytokines such as IFNγ and IL-2, which promote a robust immune system attack against the α-lactalbumin expressing cells. In the instance in which human α-lactalbumin is produced only by cells of the human breast, the proinflammatory immune response will be breast tissue specific.

In one embodiment, a method of immunizing a human patient against human α-lactalbumin is disclosed. The method comprises the step of administering to the patient an immunogenic composition comprising a polypeptide comprising human α-lactalbumin (SEQ ID NO: 1). In one aspect, the immunogenic composition comprises a polypeptide that consists essentially of human α-lactalbumin.

In one embodiment, a method of activating human T cells capable of inducing a breast tissue specific inflammatory response in a human patient is disclosed. The method comprises the step of contacting the T cells with a composition comprising isolated human dendritic cells previously exposed to a polypeptide comprising human α-lactalbumin (SEQ ID NO: 1). The activated T cells exhibit a recall response when subsequently presented with human α-lactalbumin. The recall response includes the production of proinflammatory cytokines and or chemokines, including, for example, IFNγ.

In one embodiment, a vaccine for preventing or treating breast cancer is disclosed. The vaccine comprises an immunogenic polypeptide comprising human α-lactalbumin. After administration to patients that have breast tissue producing α-lactalbumin, the vaccine induces a breast tissue specific proinflammatory immune response.

In one embodiment, a method of treating cancer in a human patient is disclosed. The method comprises the step of administering to the patient a composition comprising human α-lactalbumin, an adjuvant, and a pharmaceutically acceptable carrier, in an amount effective to induce a breast tissue specific inflammatory response in the human patient. In one embodiment, the adjuvant is GPI-0100.

In one embodiment, a method of treating cancer in a human patient is disclosed. The method comprises the step of administering to the patient a composition, the composition comprising isolated human dendritic cells that have been loaded with human α-lactalbumin, in an amount effective to induce a breast tissue specific inflammatory response in the human patient.

In one embodiment, a method of inducing a breast tissue specific inflammatory response in a human patient is disclosed. The method comprises administering to the patient a composition, the composition comprising human α-lactalbumin, an adjuvant, and a pharmaceutically acceptable carrier, wherein an increase in α-lactalbumin reactive IFNγ producing T cells is produced after administration of the composition.

In one embodiment, a method of inducing a breast tissue specific inflammatory response in a human patient is disclosed. The method comprises administering to the patient a composition, the composition comprising isolated human dendritic cells that have been loaded with human α-lactalbumin, wherein an increase in α-lactalbumin reactive IFNγ producing T cells is produced after administration of the composition.

An effective amount of human α-lactalbumin refers to an amount of human α-lactalbumin that is sufficient to be taken up by antigen presenting cells and/or activate T cells to elicit an immune response.

According to various embodiments for treatment or prevention of breast cancer, one or more booster injections of the vaccine are administered. T cells recognize discrete peptides of protein antigens presented in the context of antigen presenting molecules that are typically expressed on macrophages and dendritic cells of the immune system. Peptide recognition typically occurs following phagocytic processing of the antigen by antigen-presenting cells and loading of small peptide fragments onto Major Histocompatibility Complex (MHC) class I and/or class II molecules. After CD4+ T cells recognize peptides presented on MHC class II molecules, they proliferate rapidly and become effector T cells that may activate other immune effector cells.

CD8+ T cells are believed to recognize peptides presented by MHC class I molecules, upon which they develop into cytotoxic effector cells capable of lysing and eliminating cells that express a particular protein. CD4 and CD8 molecules serve as co-receptors because their interactions with MHC molecules. They are believed to be required for an effective T cell mediated immune response.

The ability of human α-lactalbumin to be an effective polypeptide antigen in a vaccine against breast cancer depends on whether human α-lactalbumin is sufficiently immunogenic in humans to generate a proinflammatory immune response. The immunogenicity of a particular protein, such as human α-lactalbumin, is highly unpredictable, and depends in part upon the particular amino acid sequence of the protein, its uptake and processing by antigen presenting cells into smaller peptide fragments, the availability of appropriate MHC binding sites for the processed peptide fragments, and the availability of appropriately responsive T cells with specific receptor sequences that can recognize and bind the peptide in the context of the MHC binding pocket.

EXAMPLES

Figure 1B:
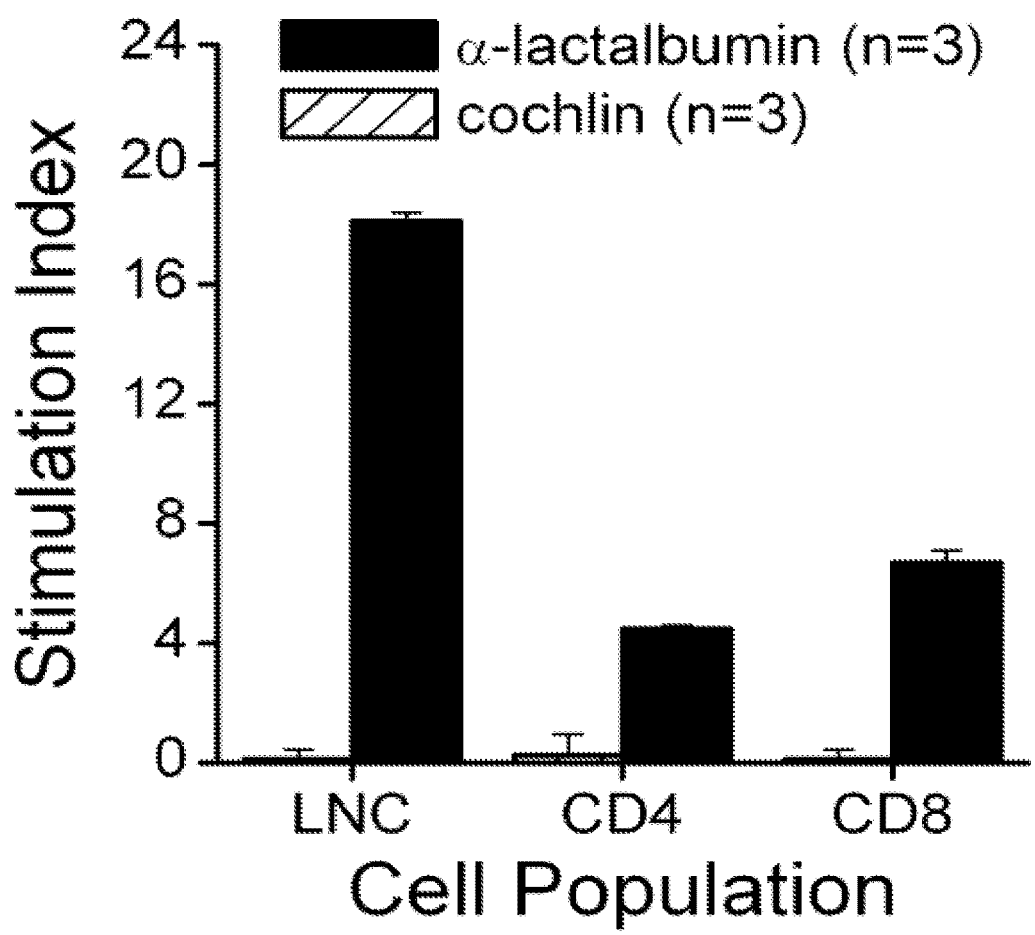
Figure 1C:
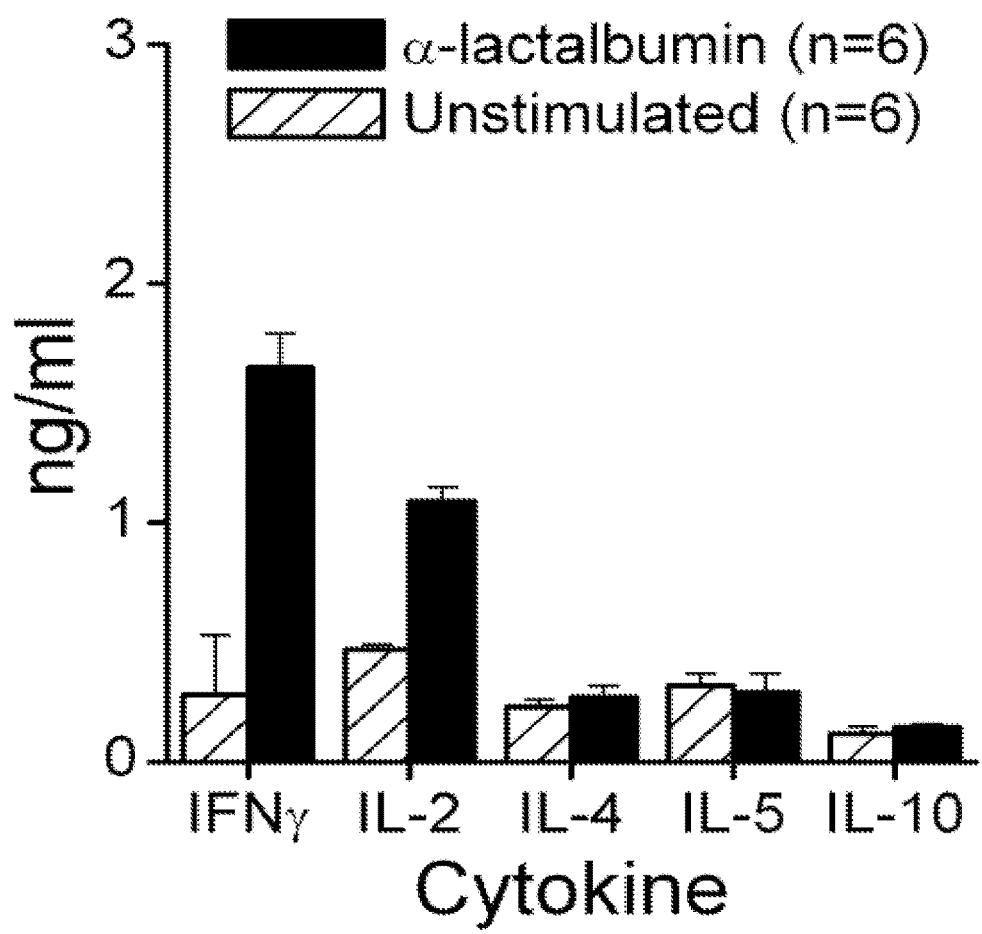

Example 1: α-Lactalbumin Immunization Activates Both CD4+ and CD8+ Proinflammatory T Cells Recombinant mouse α-lactalbumin is purified under denaturing conditions using nickel-nitrilotriacetic acid affinity chromatography followed by reverse phase HPLC. Female SWXJ mice are immunized with recombinant mouse α-lactalbumin. Ten days after immunization, lymph node cells (LNC) in the mice show a dose-dependent proliferation in recall responses to α-lactalbumin and are unresponsive to recombinant human cochlin generated in $E.\ coli$ in a virtually identical manner (see FIG. 1A). Both CD4+ and CD8+ T cells are involved in responsiveness to α-lactalbumin (see FIG. 1B). Furthermore, α-lactalbumin shows a proinflammatory phenotype involving a high production of interferon-gamma (IFNγ) and IL-2 and a low production of IL-4, IL-5, and IL-10 (see FIG. 1C).

Figure 2:
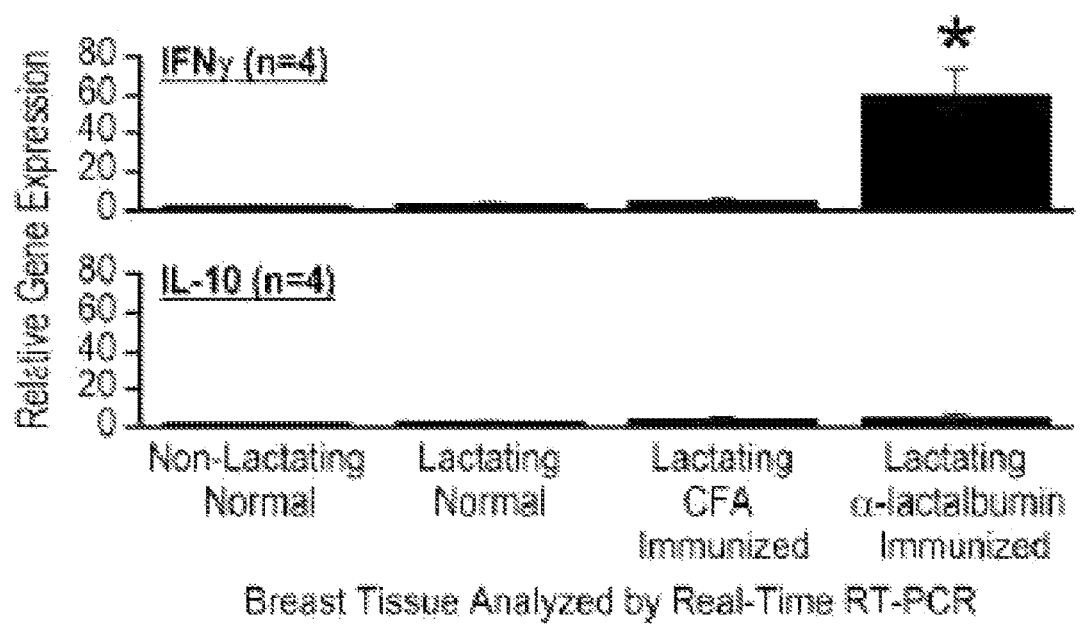
FIG. 2 shows the analysis of breast tissue during autoimmune-induced breast failure. Real-time RT-PCR analysis of lactating mammary tissue shows significantly elevated expression levels of IFNγ ($p=0.001$) but not IL-10 ($p>0.10$). All error bars show ±SEM. Each * indicates a statistically significant difference.

Example 2: Immunization of Non-Lactating Mice with α-Lactalbumin Fails to Induce Breast Inflammation Breast tissue from non-lactating mice immunized with α-lactalbumin does not demonstrate inflammatory infiltration, but instead consistently shows isolated individual CD3+ T cells migrating through breast parenchyma. However, extensive T cell infiltrates consistently occur throughout the mammary tissue of lactating mice immunized with α-lactalbumin. Breast tissue from lactating control mice immunized with CFA alone does not show inflammatory T cell infiltration. Analysis of breast infiltrating T cells by flow cytometry shows a high frequency of CD3+CD4+ T cells and CD3+CD8+ T cells expressing the CD44high activation marker. Analysis by quantitative real-time RT-PCR shows that breast tissue from lactating mice immunized with α-lactalbumin have significantly elevated expression levels of IFNγ ($p=0.001$) but not IL-10 ($p>0.10$) compared to levels expressed in breast tissue from untreated normal non-lactating or lactating mice, or from lactating mice immunized with CFA alone (see FIG. 2).

Figure 3A:
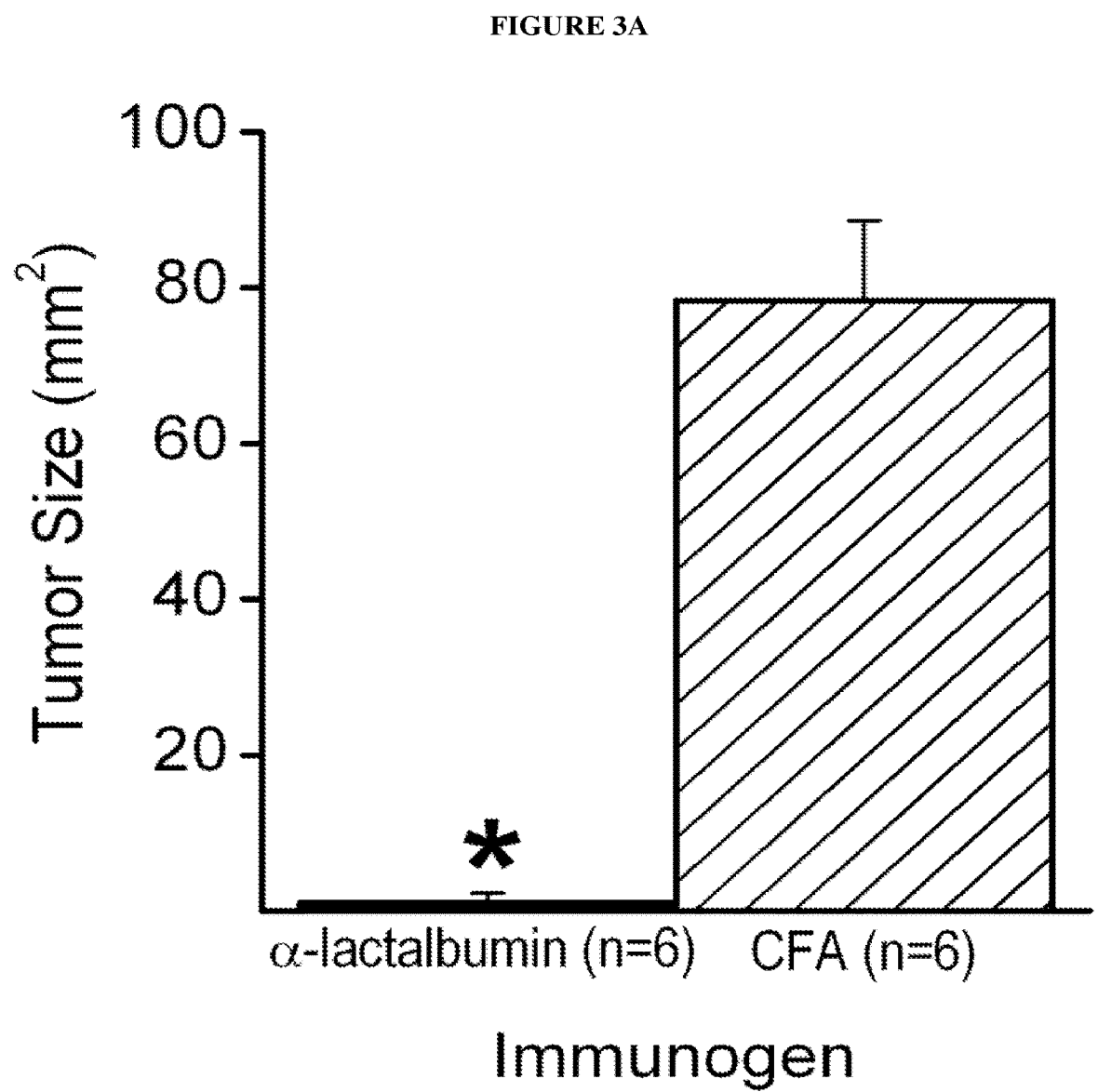
FIG. 3A shows that α-lactalbumin vaccination prophylactically inhibits growth of breast tumors. The growth of autochthonous breast tumors is significantly inhibited in ten month old MMTV-neu mice immunized with α-lactalbumin at eight weeks of age ($p=0.0004$). Growth of transplanted 4T1 tumors is significantly inhibited following prophylactic immunization with α-lactalbumin 13 days prior to tumor inoculation ($p=0.0006$.
Figure 3B:
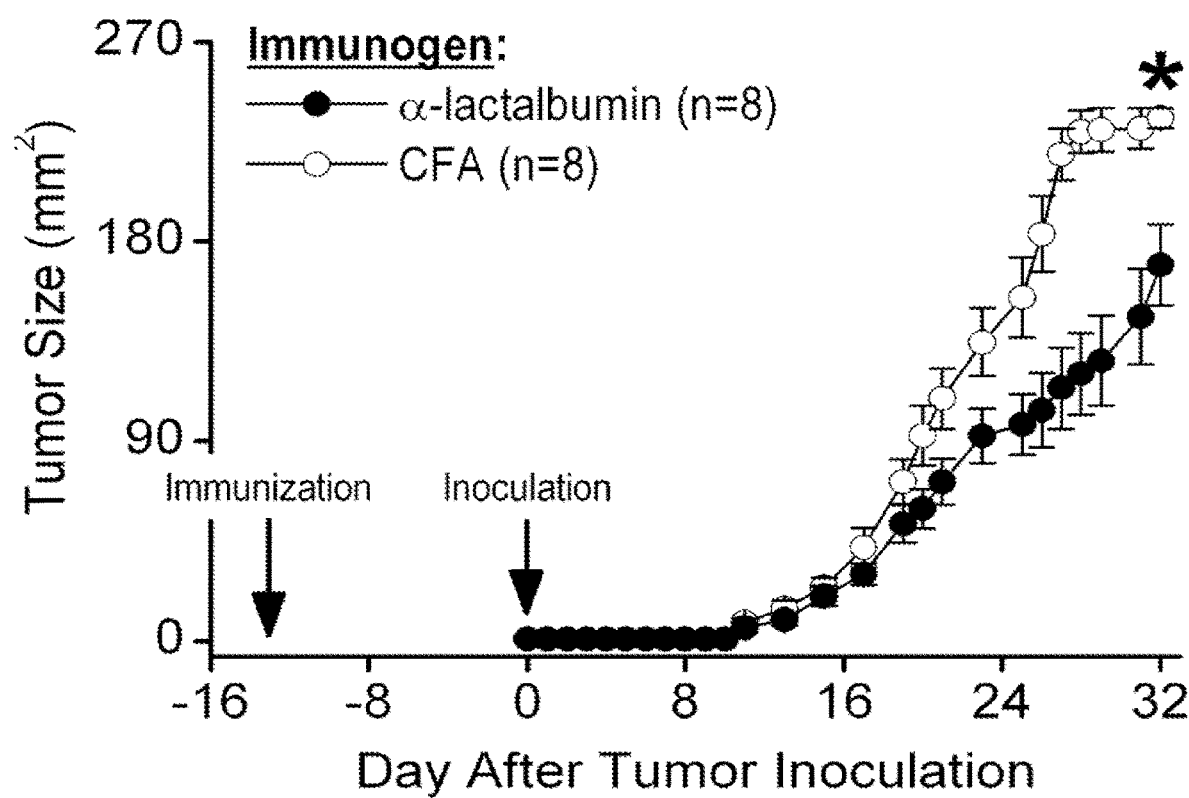
FIG. 3B). All error bars show ±SEM. Each* indicates a statistically significant difference.

Example 3: Prophylactic α-Lactalbumin Vaccination Inhibits Growth of Breast Tumors MMTV-neu mice express the unactivated neu (ErbB2 or HER2/neu) protooncogene under the regulation of the long terminal repeat of mouse mammary tumor virus (MMTV) and show a 50% incidence of spontaneous mammary tumors by 205 days of age. Eight week old MMTV-neu mice are immunized with either α-lactalbumin in CFA or with CFA alone. All mice are euthanized when the first tumor reached 17 mm in diameter (at around 10 months of age). Upon completion of the experiment, all CFA-immunized control mice develop breast tumors upon. In comparison, none of the mice immunized with α-lactalbumin show any detectable mammary tumors ($p=0.0004$; see FIG. 3A). Prophylactic vaccination with α-lactalbumin is also effective against transplantable 4T1 tumors. BALB/c mice immunized with α-lactalbumin 13 days prior to inoculation with 4T1 tumor cells exhibit significant growth inhibition ($p=0.0006$; see FIG. 3B).

Figure 4A:
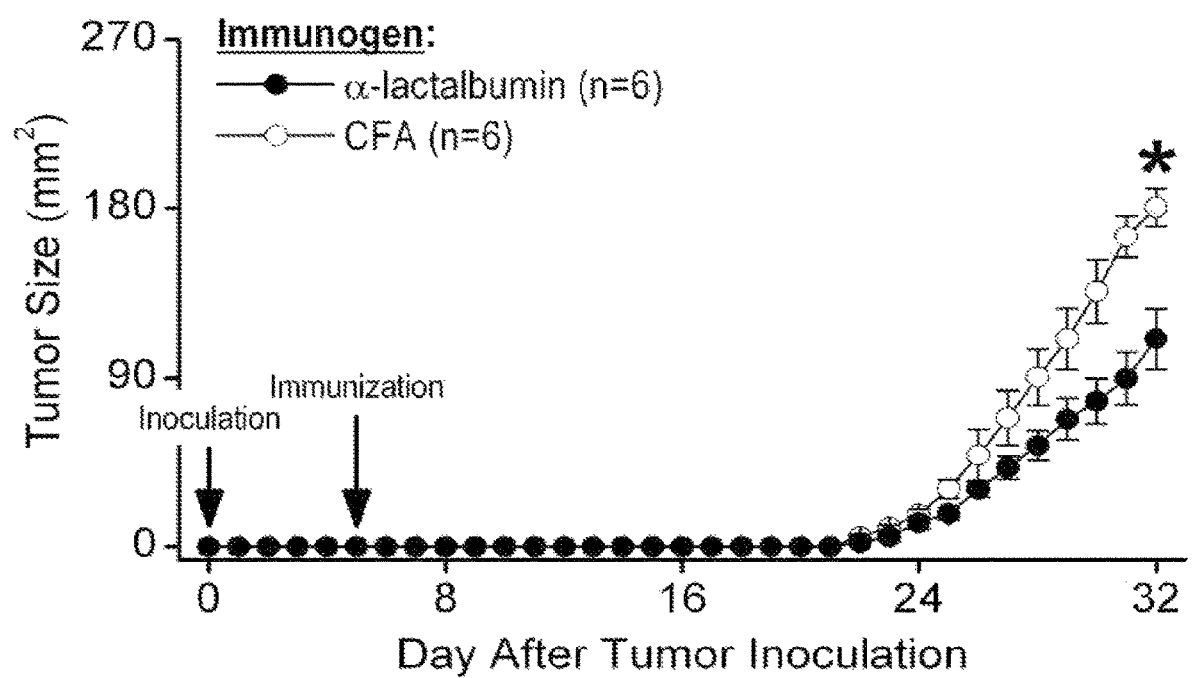
FIG. 4A shows that α-lactalbumin vaccination treats established growing transplanted breast tumors. Significant inhibition of 4T1 tumor growth occurs following α-lactalbumin immunization at 5 days after tumor inoculation ($p<0.01$) and at 13 days after tumor inoculation ($p<0.01$.
Figure 4B:
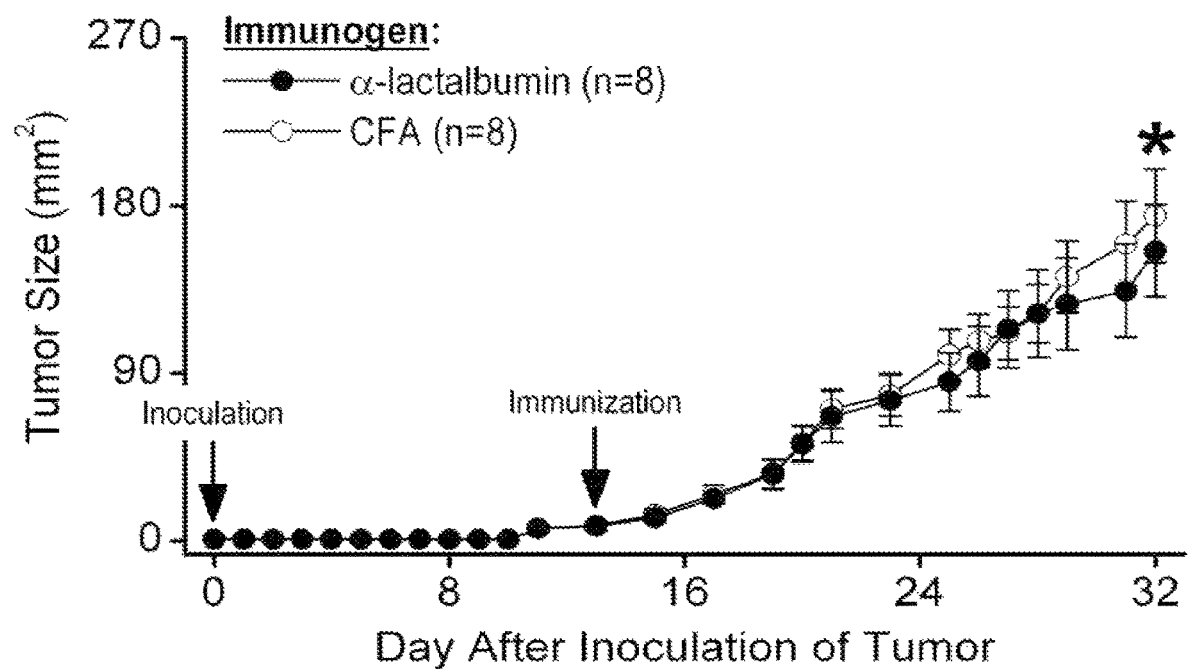
FIG. 4B), but not at 21 days after tumor inoculation ($p>0.10$.
Figure 4C:
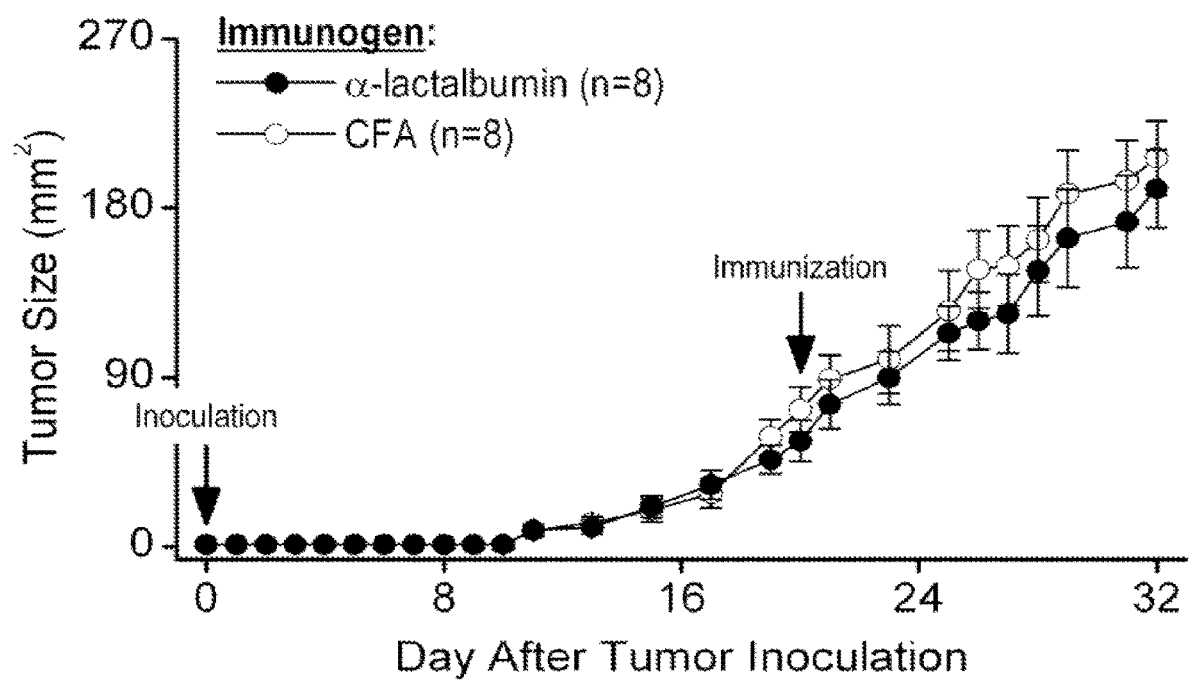
FIG. 4C). All error bars show ±SEM. Each* indicates a statistically significant difference.

Example 4: α-Lactalbumin Vaccination Inhibits Growth of Established Transplanted 4T1 Breast Tumors Following subcutaneous inoculation of BALB/c mice with $2\times10^4$ 4T1 tumor cells, tumors are well established within 5 days after inoculation and palpable tumors are present within 2 to 3 weeks after inoculation. After inoculation with 4T1 tumor cells, vaccination with α-lactalbumin is performed at 5 days after inoculation, at 13 days after inoculation, and at 21 days after inoculation. A significant inhibition of tumor growth is observed at the 5-day vaccination ($p<0.01$; see FIG. 4A) and at the 13-day vaccination ($p<0.01$; see FIG. 4B) but not at the 21-day vaccination (see FIG. 4C). The lack of tumor growth inhibition in mice vaccinated 21 days after inoculation may be due to the shortened 11-day observation period between the time of immunization and the time when tumors reach the maximum size mandating euthanasia.

Figure 5:
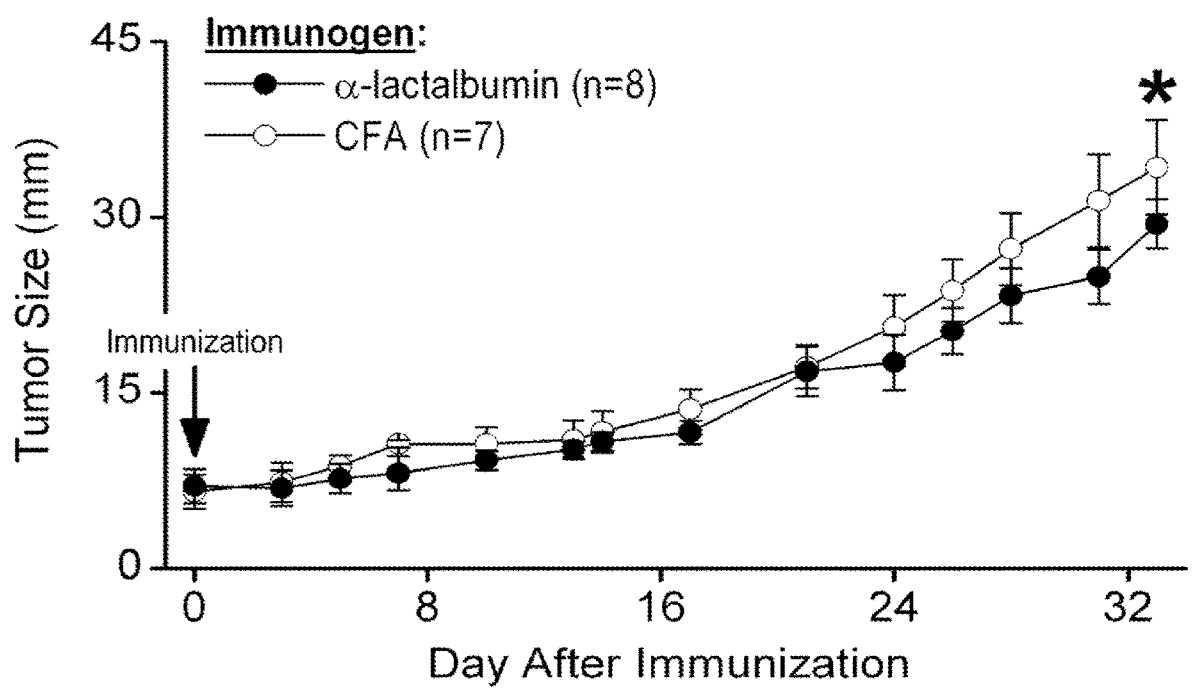
FIG. 5 shows that α-lactalbumin vaccination treats established growing autochthonous breast tumors. Significant inhibition ($p<0.0006$) in the growth of extremely aggressive autochthonous tumors occurs following α-lactalbumin immunization of MMTV-PyVT transgenic mice at 6 weeks of age. Due to massive multifocal tumor growth, tumors in MMTV-PyVT mice are amenable to measurement in only one direction. The longest measurements on all ten MMTV-PyVT tumors are added to calculate total tumor load in mm on each day.

Example 5: α-Lactalbumin Vaccination Inhibits Growth of Established Autochthonous Breast Tumors MMTV-PyVT transgenic mice demonstrate loss of lactational ability coincident with transgene expression and develop palpable very aggressively growing mammary tumors by 5 weeks of age. In this example, MMTV-PyVT transgenic mice are vaccinated at 6 weeks of age with α-lactalbumin. Significant inhibition in the growth of very aggressive established autochthonous tumors in MMTV-PyVT is observed ($p<0.0006$; see FIG. 5). Thus, α-lactalbumin vaccination indicates effective protection and therapy against breast tumor growth and is particularly effective when immunization occurs prior to the appearance of palpable tumors in MMTV-PyVT transgenic mice.

Figure 6A:
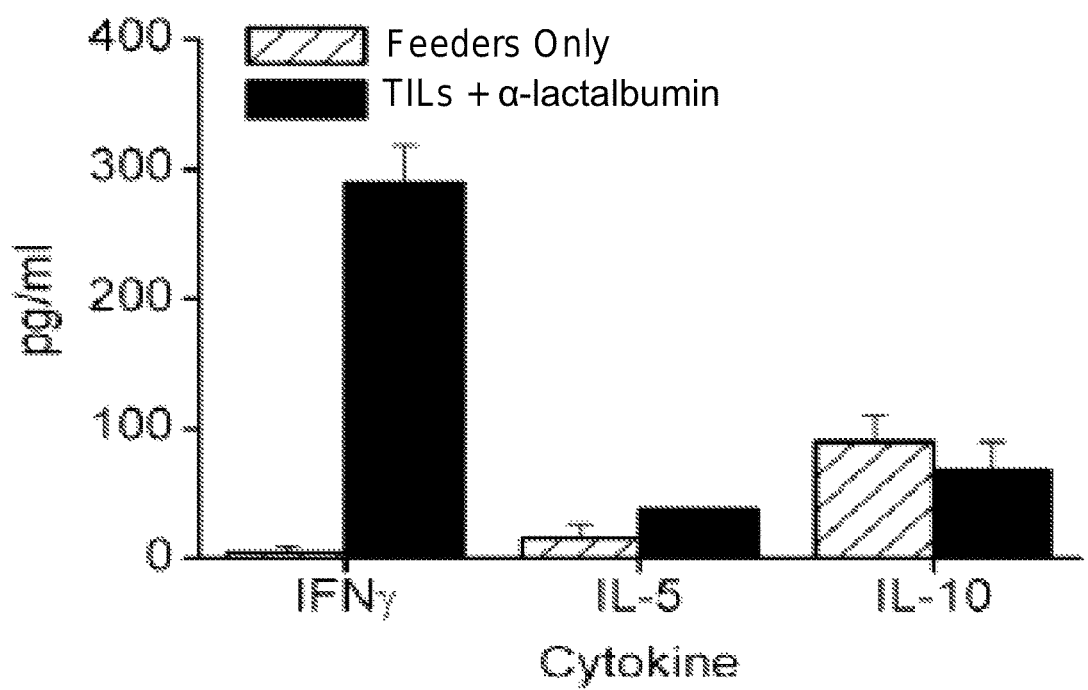
FIG. 6A shows that α-lactalbumin-specific T cells induce tumor inflammation and cytotoxicity. Recall responses to α-lactalbumin as measured by ELISA demonstrate a type-1 proinflammatory phenotype involving high production of IFNγ compared to IL-5 and IL-10. ELISPOT analysis of TILs shows that CD4+ rather than CD8+ T cells produce IFNγ (FIG. 6B). Death of cultured 4T1 tumor cells is inhibited by treatment of cultured α-lactalbumin primed LNC with antibodies specific for mouse CD8, indicating that CD8+ T cells mediate 4T1 specific cytotoxicity (FIG. 6C).
Figure 6B:
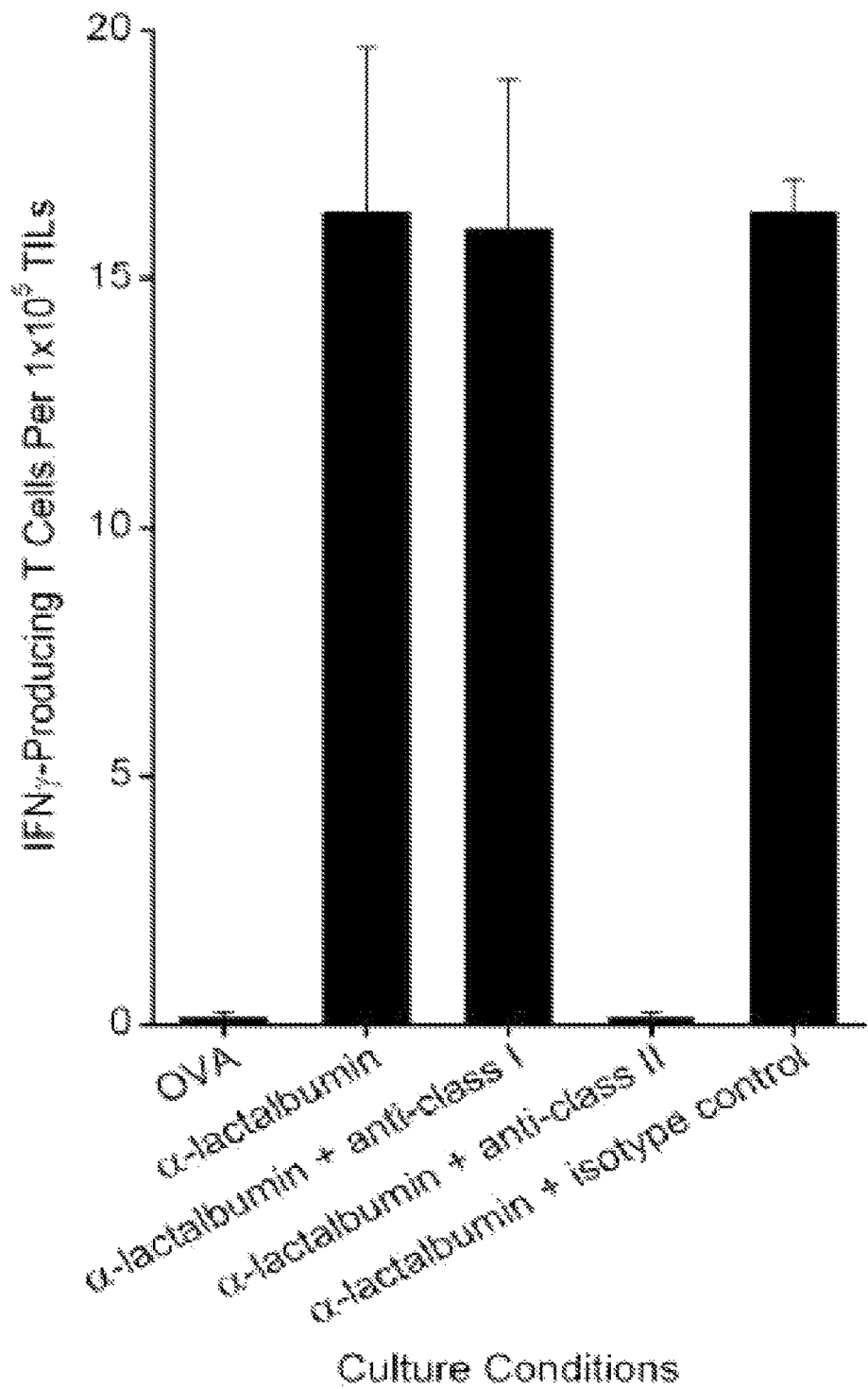
Figure 6C:
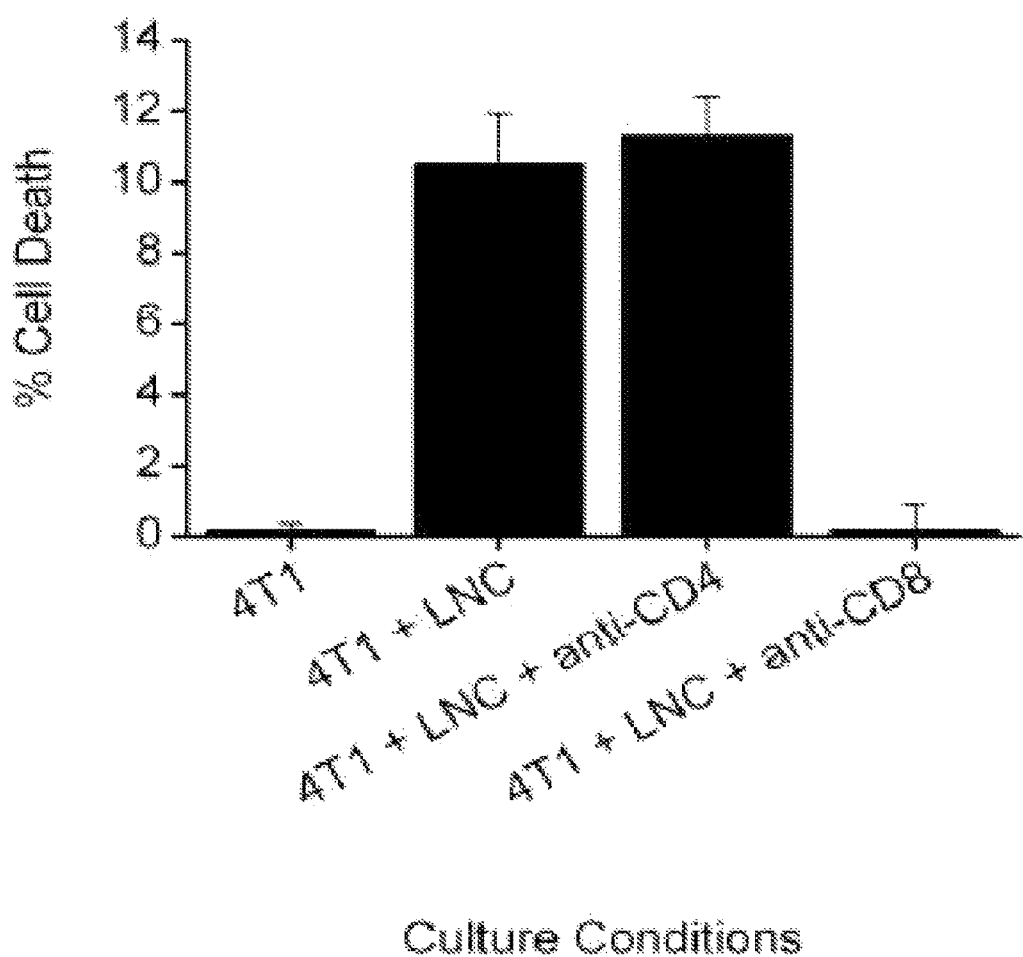

Example 6: α-Lactalbumin-Specific T Cells Induce Tumor Inflammation and Cytotoxicity BALB/c mice are vaccinated with α-lactalbumin and inoculated with 4T1 cells.
Approximately 32 days after inoculation, tumors in the BALB/c mice show extensive infiltration of CD3+ T cells. In comparison, these inflammatory infiltrates do not occur in tumors from control mice immunized with CFA. Flow cytometry analysis of tumor infiltrating lymphocytes (TILs) show a predominance of CD4+(64.3%) T cells compared to CD8+ (14.4%) Tcells.
Furthermore, recall responses to 50 μg/ml α-lactalbumin as measured by ELISA demonstrate a type-1 proinflammatory phenotype involving high production of IFNγ compared to IL-5 and IL-10 (see FIG. 6A). ELISPOT analysis of TILs shows that CD4+ rather than CD8+ T cells are produced the IFNγ since its secretion by cultured T cells is inhibited by treatment with class II but not class I specific antibodies (see FIG. 6B). However, death of cultured 4T1 tumor cells is inhibited by treatment of cultured α-lactalbumin primed LNC with antibodies specific for mouse CD8 but not CD4 (see FIG. 6C). This result indicates that CD8+ T cells mediate 4T1 specific cytotoxicity.

Figure 7A:
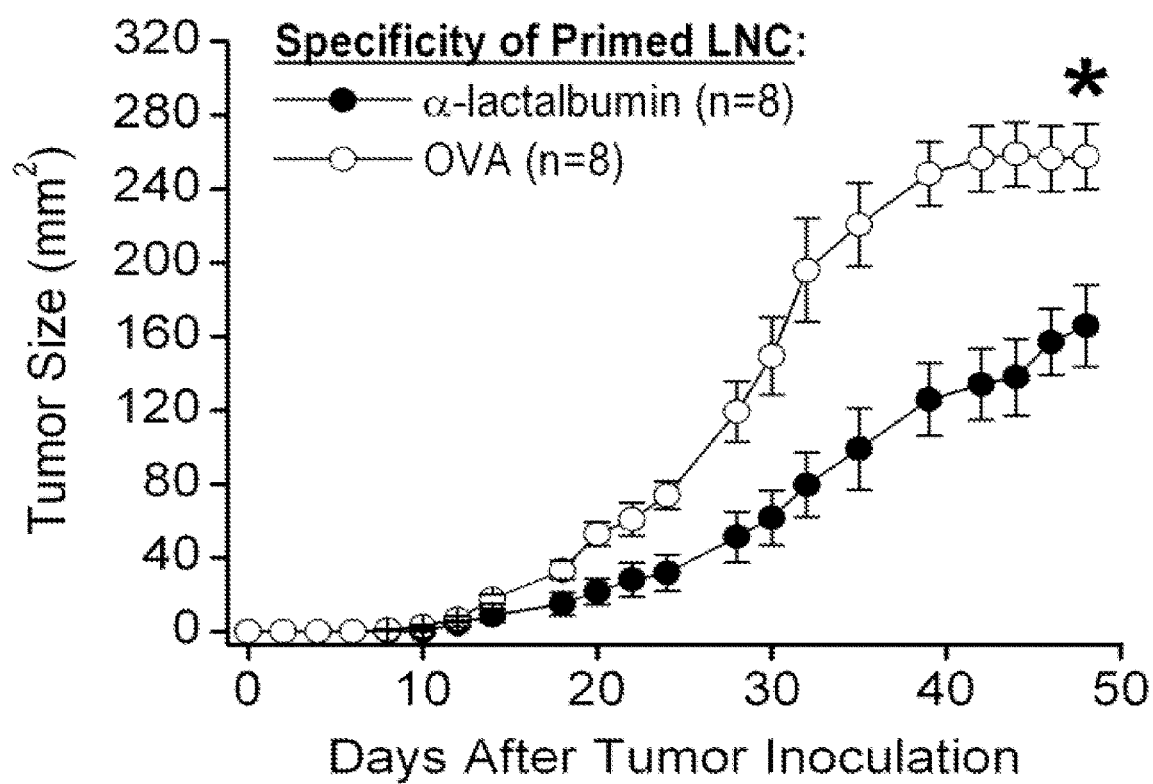
FIG. 7A shows that inhibition of tumor growth by α-lactalbumin vaccination is mediated by T cells. The transfer of α-lactalbumin primed LNC into naïve recipient BALB/c mice on the same day as inoculation with 4T1 tumors results in a) a significant inhibition of tumor growth ($p<0.0001$); b) a significant decrease in incidence of tumor bearing mice ($p<0.03$.
Figure 7B:
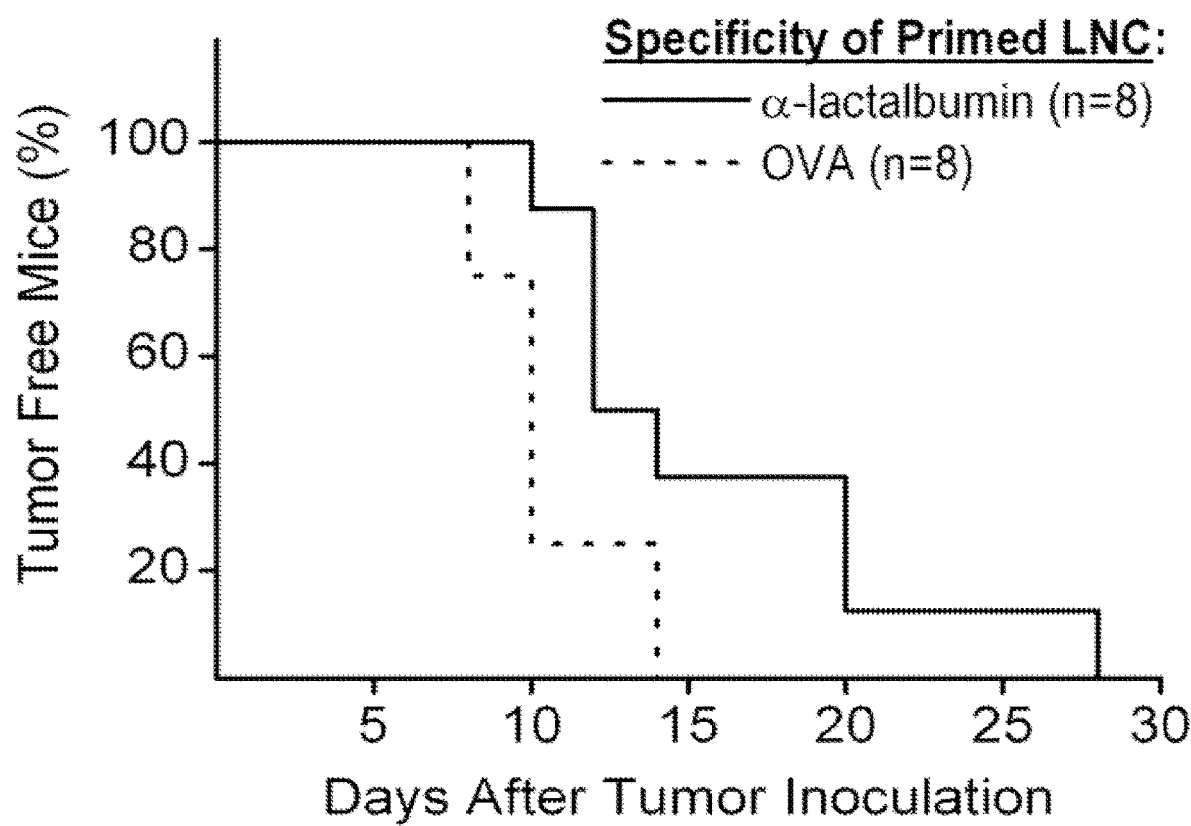
FIG. 7B); and c) a significant decrease in final tumor weight ($p<0.0008$.
Figure 7C:
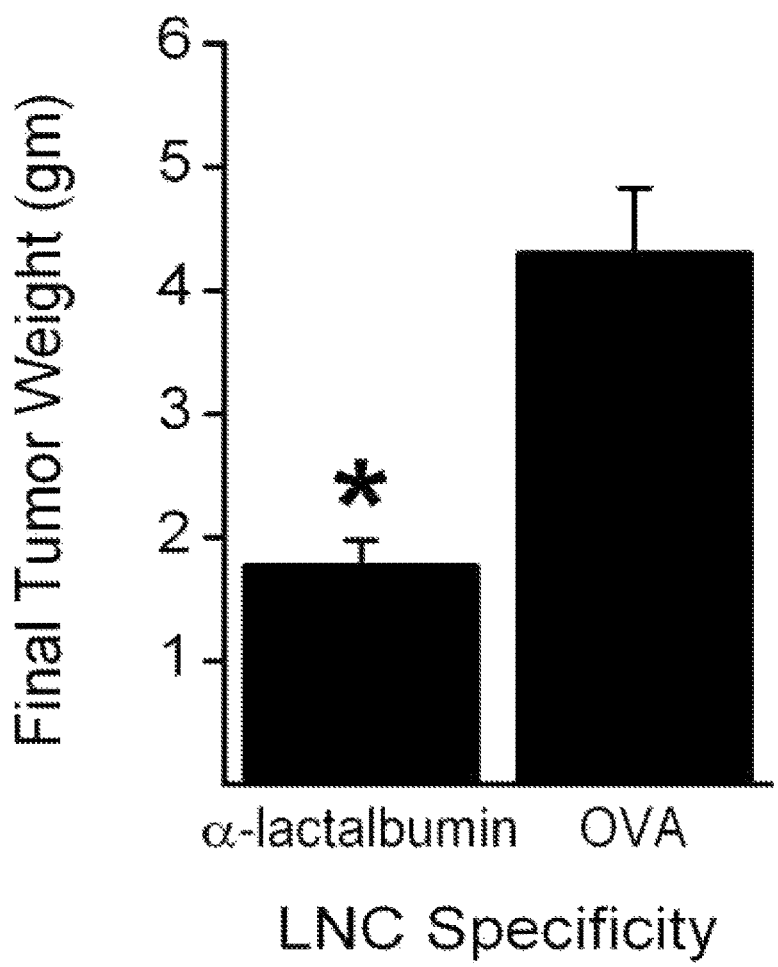
FIG. 7C). Compared to ovalbumin (OVA) primed LNC, significant tumor growth inhibition occurs in naïve mice receiving either CD4+ T cells ($p=0.002$.
Figure 7D:
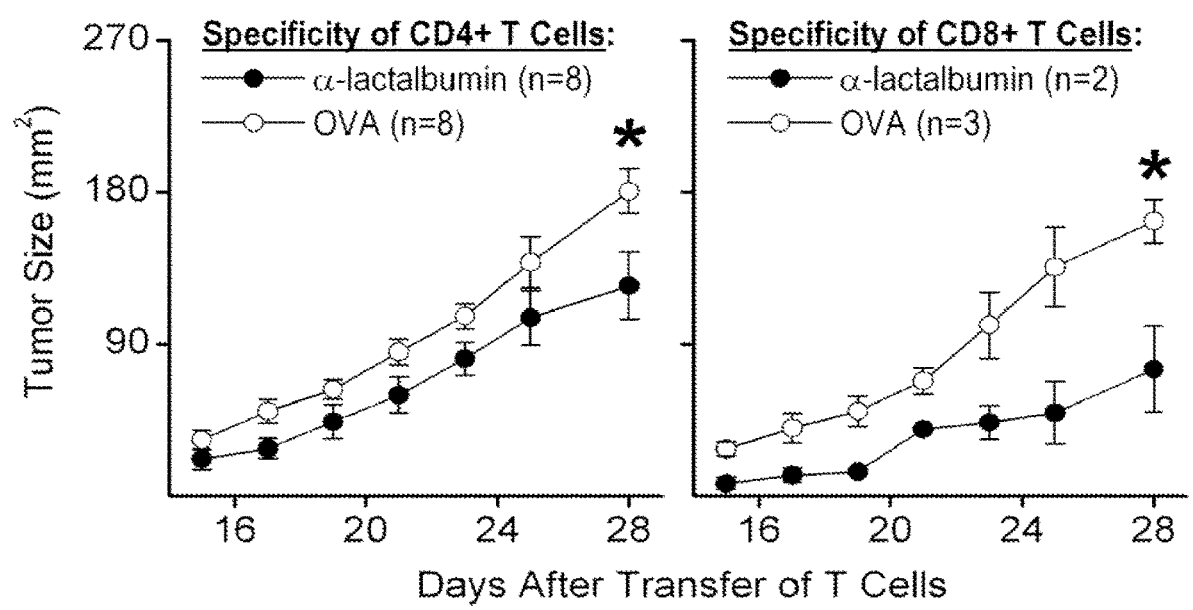
FIG. 7D left panel) or CD8+ T cells ($p=0.003$.

Example 7 Inhibition of Breast Tumor Growth by α-Lactalbumin Vaccination is Mediated by T Cells On the same day, naïve recipient BALB/c mice are inoculated with 4T1 tumors and α-lactalbumin-primed LNC. A significant inhibition of tumor growth is observed in these mice ($p<0.0001$; see FIG. 7A). Furthermore, the incidence of tumor bearing mice is significantly decreased in this example ($p<0.03$; see FIG. 7B) and the final tumor weight is also significantly decreased ($p<0.0008$; see FIG. 7C).
Naïve mice further received a) CD4+ T cells enriched by magnetic bead separation from α-lactalbumin-primed LNC, b) CD8+ T cells enriched by magnetic bead separation from α-lactalbumin-primed LNC, or c) control ovalbumin (OVA)-primed LNC. Significant tumor growth inhibition is observed in the mice receiving the CD4+ T cells enriched by magnetic bead separation from α-lactalbumin-primed LNC ($p=0.002$; see FIG. 7D, left panel) and the CD8+ T cells enriched by magnetic bead separation from α-lactalbumin-primed LNC ($p=0.003$; see FIG. 7D, right panel) compared to OVA-primed LNC. This example indicates that activated CD4+ and CD8+ TILs mediate the protective and therapeutic effects of α-lactalbumin vaccination on breast tumor growth.

Example 8: Availability of α-Lactalbumin Responsive T Cells in Females

T cell repertoire availability and magnitude is assessed in peripheral blood mononuclear cells (PBMC) by in vitro priming against α-lactalbumin and measurement of the resulting antigen-specific frequencies of IFNγ-producing T cells. Monocyte derived DCs were prepared from PBMC taken from a 29 year-old female patient. Adherent cell selection was followed by culture in X-VIVO media (Bio-Whittaker, Walkersville, MD) with 500 U/ml rhGMCSF and rhIL-4 (Peprotech, Rocky Hill, NJ). Six days after initiation of culture, DCs were pulsed with 75 μg/ml of purified recombinant human α-lactalbumin (rhα-lactalbumin) and were washed extensively 48 hours later. The washed DCs were co-cultured with nylon wool purified naive T cells from the same donor at a ratio of 1:5 (DCs to T cells). Approximately 72 hours after co-culture, in vitro primed T cells and unprimed T cells from the same donor were enriched by passage through nylon wool and re-cultured with γ-irradiated (3000 rads) PBMC as feeder cells at a ratio of 1:10 (feeders to T cells) on ELISPOT plates (Polyfiltronics, Rockland, MA) pre-coated with mouse anti-human IFNγ capture antibody (#M-700A; Endogen, Cambridge, MA). Frequencies of α-lactalbumin reactive IFNγ producing T cells were determined 48 hours later using secondary biotinylated mouse anti-human IFNγ (#M701; Endogen) and resolution of ELISPOTS using an automated Immunospot Satellite Analyzer (Cellular Technology, Cleveland, OH).

Figure 8:
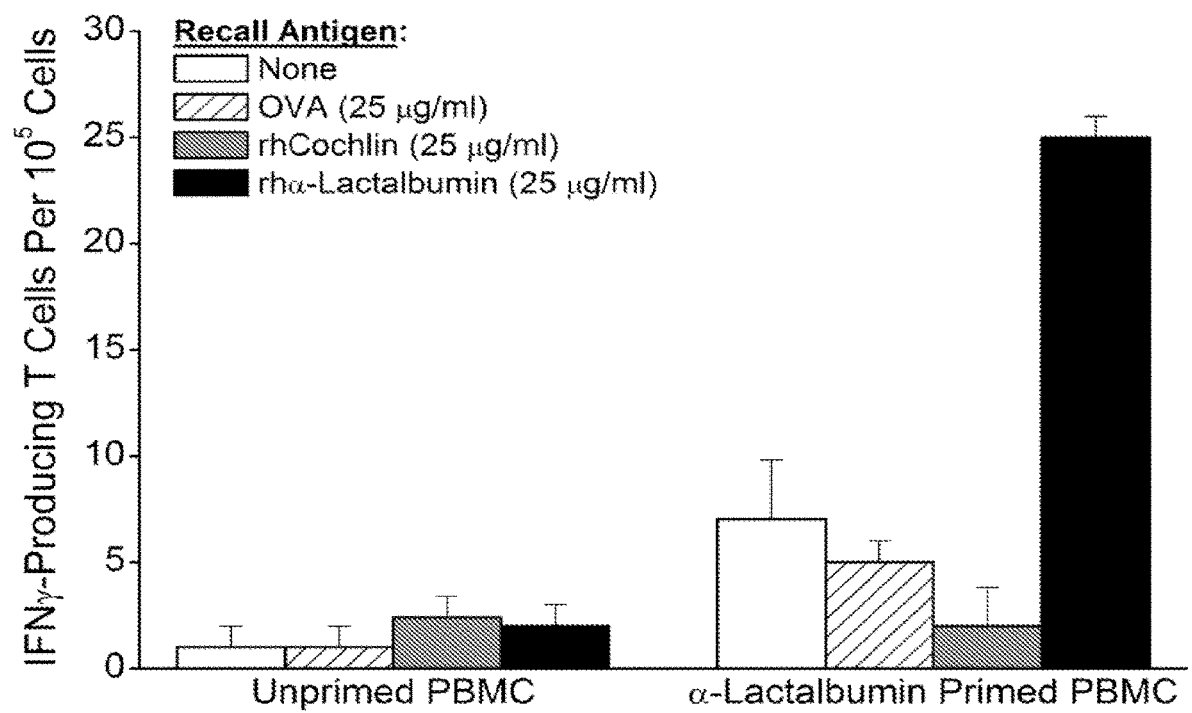
FIG. 8 shows in vitro priming of human peripheral blood mononuclear cells (PBMC) T cell using blood derived dendritic cells (DCs) to test for the availability of a human α-lactalbumin-reactive T cell repertoire. Priming of PMBCs with α-lactalbumin results in an increased frequency of IFNγ producing T cells upon subsequent presentation of α-lactalbumin (recall response).

After priming with α-lactalbumin, the PMBCs demonstrate an increased frequency of IFNγ producing T cells (see FIG. 8) upon subsequent exposure to α-lactalbumin (recall response). The observed response is antigen specific, as recall antigens OVA and recombinant human cochlin (rmCochlin), an inner ear protein generated in transduced E. coli in a manner similar to the production of recombinant human α-lactalbumin, do not elicit an increase in IFNγ producing T cells.

Taken together, the results described herein show that show that 1) immunization with α-lactalbumin activates both CD4+ and CD8+ proinflammatory T cells; 2) immunization of non-lactating mammals with α-lactalbumin fails to induce breast inflammation; 3) prophylactic α-lactalbumin vaccination inhibits growth and incidence of breast tumors; and 4) α-lactalbumin vaccination inhibits growth of established tumors. α-lactalbumin immunization provides a safe and effective vaccination in several murine breast cancer models.

Importantly, it is also demonstrated herein that human α-lactalbumin is sufficiently immunogenic in humans to activate T cells and elicit a proinflammatory immune recall response. Thus, immunization of humans with human α-lactalbumin has the ability to provide a safe and effective vaccine for human breast cancer.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present invention.

```
                                   SEQUENCE LISTING

Sequence total quantity: 1
SEQ ID NO: 1           moltype = AA  length = 123
FEATURE                Location/Qualifiers
source                 1..123
                       mol_type = protein
                       organism = Homo sapiens
SEQUENCE: 1
KQFTKCELSQ LLKDIDGYGG IALPELICTM FHTSGYDTQA IVENNESTEY GLFQISNKLW  60
CKSSQVPQSR NICDISCDKF LDDDITDDIM CAKKILDIKG IDYWLAHKAL CTEKLEQWLC  120
EKL                                                                123
```

What is claimed is:

1. A method of immunizing a human patient against a human α-lactalbumin, the method comprising the step of administering to the patient an immunogenic composition comprising human α-lactalbumin (SEQ ID NO: 1).

2. The method of claim 1, wherein T cells are activated after administration of the immunogenic composition to the patient.

3. The method of claim 2, wherein the T cells are CD4+.

4. The method of claim 2, wherein the T cells are CD8+.

5. The method of claim 1, wherein a proinflammatory immune response is induced by subsequent encounter of immune cells with α-lactalbumin.

6. The method of claim 5, wherein the proinflammatory immune response comprises production of INFγ by T cells.

7. The method of claim 5, wherein the proinflammatory immune response is breast tissue specific.

* * * * *

UNITED STATES PATENT AND TRADEMARK OFFICE
CERTIFICATE OF CORRECTION

| | | |
|---|---|---|
| PATENT NO. | : 12,370,244 B2 | Page 1 of 1 |
| APPLICATION NO. | : 18/063999 | |
| DATED | : July 29, 2025 | |
| INVENTOR(S) | : Vincent Tuohy et al. | |

It is certified that error appears in the above-identified patent and that said Letters Patent is hereby corrected as shown below:

In the Specification

On Column 1, Lines 5-8 please replace the first paragraph as follows:
GOVERNMENT RIGHTS
This invention was made with government support under AI051837, CA140350 and DC006422 awarded by the National Institutes of Health. The government has certain rights in the invention.

Signed and Sealed this
Thirtieth Day of September, 2025

John A. Squires
*Director of the United States Patent and Trademark Office*